United States Patent
Howgill (10) Patent No.: US 8,459,253 B2
(45) Date of Patent: Jun. 11, 2013

(54) DOSE COUNTER

(75) Inventor: Stephen J. Howgill, Leicestershire (GB)

(73) Assignee: 3M Innovative Properties Company, St. Paul, MN (US)

( * ) Notice: Subject to any disclaimer, the term of this patent is extended or adjusted under 35 U.S.C. 154(b) by 591 days.

(21) Appl. No.: 12/593,812

(22) PCT Filed: Feb. 25, 2008

(86) PCT No.: PCT/US2008/054833
§ 371 (c)(1),
(2), (4) Date: Apr. 28, 2010

(87) PCT Pub. No.: WO2008/121459
PCT Pub. Date: Oct. 9, 2008

(65) Prior Publication Data
US 2010/0229855 A1   Sep. 16, 2010

(30) Foreign Application Priority Data
Apr. 2, 2007 (GB) .................................. 0706405.8

(51) Int. Cl.
*A61M 11/00* (2006.01)
(52) U.S. Cl.
USPC ................... 128/200.23; 128/205.23; 222/36
(58) Field of Classification Search
USPC   128/200.23, 203.12, 203.15, 205.23; 222/36, 222/38, 48, 402.1, 402.13
See application file for complete search history.

(56) References Cited

U.S. PATENT DOCUMENTS

| | | | |
|---|---|---|---|
| 4,668,218 A | 5/1987 | Virtanen | |
| 5,349,945 A | 9/1994 | Wass et al. | |
| 5,870,117 A | 2/1999 | Moore | |
| 5,871,007 A | 2/1999 | Clark, Jr. | |
| 5,988,496 A | 11/1999 | Bruna | |
| 6,446,627 B1 | 9/2002 | Bowman et al. | |
| 6,655,381 B2 | 12/2003 | Keane et al. | |
| 6,752,153 B1 | 6/2004 | Eckert | |
| 6,907,876 B1 | 6/2005 | Clark et al. | |
| 7,156,258 B2 | 1/2007 | Eckert | |

(Continued)

FOREIGN PATENT DOCUMENTS

| | | |
|---|---|---|
| EP | 0 480 488 | 4/1992 |
| GB | 2 191 032 | 12/1987 |

(Continued)

OTHER PUBLICATIONS

Form PCT/ISA/210, International Search Report from WO 2008/121459.

*Primary Examiner* — Steven Douglas (57) ABSTRACT

A dose counting device for use with a medicinal metered dose dispensing device, the device including an actuator having at least one finger that is designed for reciprocal movement comprising an outward stroke and a return stroke, an annular member having a helical thread segment formed about a circumferential arc on a part of its surface, and a drive nut positioned around a radial cross-section of the annular member and having an internal helical rib engaged with said helical thread segment on the annular member whereby rotation of the drive nut about the circumferential arc of the annular member results in rotational movement of the annular member, the outer surface of the drive nut comprising one or more driving surfaces for engagement by said at least one finger on the actuator during said reciprocal movement to cause rotation of the drive nut.

15 Claims, 9 Drawing Sheets

U.S. PATENT DOCUMENTS

| | | |
|---|---|---|
| 7,195,134 B2 | 3/2007 | Ouyang et al. |
| 7,819,075 B2 * | 10/2010 | Bowman et al. ............... 116/307 |
| 8,074,643 B2 * | 12/2011 | Scarrott et al. ........... 128/200.23 |
| 8,157,128 B2 * | 4/2012 | Blacker et al. .................. 222/36 |
| 8,181,591 B1 * | 5/2012 | Gulka et al. .................. 116/285 |
| 2002/0170928 A1 | 11/2002 | Grychowski et al. |
| 2002/0189611 A1 | 12/2002 | Greenwood et al. |
| 2002/0195102 A1 | 12/2002 | Rand et al. |
| 2004/0065326 A1 | 4/2004 | MacMichael et al. |
| 2005/0087191 A1 | 4/2005 | Morton et al. |
| 2005/0126469 A1 | 6/2005 | Lu |

FOREIGN PATENT DOCUMENTS

| | | |
|---|---|---|
| GB | 2 348 928 | 10/2000 |
| WO | WO 93/21980 | 11/1993 |
| WO | WO 96/39337 | 12/1996 |
| WO | WO 02/091293 | 11/2002 |
| WO | WO 2004/013582 | 2/2004 |
| WO | WO 2005/084736 | 9/2005 |
| WO | WO 2006/004498 | 1/2006 |
| WO | WO 2006/027313 | 3/2006 |
| WO | WO 2006/054083 | 5/2006 |
| WO | WO 2006/062450 | 6/2006 |

* cited by examiner

DOSE COUNTER

CROSS REFERENCE TO RELATED APPLICATIONS

This application is a national stage filing under 35 U.S.C. 371 of PCT/US2008/054833 filed Feb. 25, 2008, which claims priority to Great Britain Application No. 0706405.8, filed Apr. 2, 2007, the disclosure of which is incorporated by reference in its/their entirety herein.

FIELD OF INVENTION

This invention relates to a dose counting device, referred to in the following generally as a dose counter, in which movement of an actuator is converted to rotational movement of an annular member. Such a dose counter is particularly useful as a counter mechanism for medicinal metered dose dispensing devices such as inhaler devices. Such a dose counter may be suitably utilized as a dose indicator, for example by suitably arranging the dose counter to provide an indication of the number of doses nominally remaining in and/or dispensed from such a dispensing device.

BACKGROUND TO THE INVENTION

Certain devices that are operated by a reciprocating element, e.g. a button, require the presence of a counting device in order to provide an indication of the extent of use. Known counting devices range from complex electrical devices providing a visual digital display to simple mechanical devices having a sliding scale to display the count or extent of use.

Many types of medicines may be administered by nasal or oral inhalation. In many cases the medicament is formulated with a suitable propellant and other components and charged in an aerosol vial. The aerosol vial is fitted, typically by means of a valve ferrule, with a valve which comprises a metering chamber such that each operation of the valve, typically through depression of a valve stem, dispenses a predetermined measured quantity of medicament. The aerosol vial is inserted into an adapter having a mouthpiece or a port adapted for nasal use and the medicament is dispensed simultaneously with inhalation.

There are two general types of adapter used with such aerosol vials. A breath-actuated adapter comprises a mechanism that allows the patient to prime the device, and then the aerosol is fired automatically in response to the patient inhaling through the mouthpiece or nasal port. A second type of adapter is a press-and-breathe adapter in which the patient fires the device by manually pressing the aerosol vial whilst inhaling through the mouthpiece or nasal port.

The aerosol vial is initially charged with a known quantity of medicament, a metered dose of which is dispensed each time the valve is operated. Counting the number of operations of the valve will give an indication of the total medicament dispensed and hence of the amount of medicament remaining in the vial. The metering is normally accurate, but incorrect actuation of the valve occasionally results in a reduced dose. However, the dose cannot exceed the predetermined metered quantity when the aerosol device is fired. Therefore, counting the number of doses used is a safe basis for computing the number of doses remaining because any error will indicate the presence of fewer doses than are actually present. It is highly desirable that the patient be given an indication that the contents of the vial are depleted before the vial is actually empty, to prevent the patient attempting to use an empty inhaler at a time when the patient is under stress. Accordingly, it is desirable to incorporate some form of counting device on the aerosol vial or adapter that would give an appropriate indication before the vial becomes empty.

A conventional aerosol valve is operated by causing a valve stem to be depressed relative to the valve body. A convenient means of counting the number of discharges from the aerosol vial is to convert the relative reciprocatory movement between the valve stem and the valve body into a one-way movement of some form of counting device or indicator. If the number of doses contained within the vial were relatively small it would be possible to use linear movement of the vial to index a simple indicator band along and so mark the progression from "full" to "empty". Such a counting means need only comprise a ratchet device and a toothed indicator rack moving in the direction parallel to the relative reciprocal motion between the valve stem and the valve body. However, the number of doses in an aerosol vial is normally at least fifty and often two hundred. Accordingly, in practice, the total linear movement of such a rack would be far too great to be accommodated in a normal inhaler unless each incremental step of the rack was very small. However, tiny incremental steps require firstly that only a small fraction of the total reciprocatory movement of the valve stem is converted into rack movement and secondly that very fine teeth must be moulded on both mating parts. These requirements are not easy to fulfil economically and on a mass production basis.

In addition to the ability to accurately count many doses it is important that the counting device is not susceptible to false counting, or otherwise presenting incorrect information. False counting can occur due to inaccuracies or malfunctioning of the components of the device, movement of the valve stem insufficient to fire a dose, repeated reciprocation of the valve stem before it has returned to its rest position, back rotation of the indicator during the return stroke of the valve stem, or movement of the dose counter assembly due to vibrations when the device is carried in a pocket or handbag etc. Another design criterion for dose counters used with inhalation devices is that the impact on the airflow through the device must be minimal, so that the aerolisation characteristics of the doses are not affected by incorporating the dose counter into the device.

There have been numerous proposals for inhaler counting devices.

U.S. Pat. No. 5,349,945, WO06/062450, US20020170928 and US20050087191 disclose dose counters incorporating a worm and rack mechanism.

US20050126469, WO93/21980, U.S. Pat. No. 5,871,007, U.S. Pat. No. 6,907,876, GB2348928, US20020189611, U.S. Pat. No. 4,668,218 and WO06/054083 disclose devices in which a cylindrical member having a helix or spiral is used to convert rotary motion into another, generally linear, motion.

WO02/91293, U.S. Pat. No. 6,752,153, GB2348928, WO96/39337, WO06/054083, EP0480488, FR2842905 and U.S. Pat. No. 5,871,007 disclose devices comprising one or more flexible members that operate a mechanism when loaded and spring back when unloaded.

Other counting devices that include some form of ratchet mechanism are disclosed in U.S. Pat. No. 6,446,627, GB2191032, WO06/027313, US20040065326, WO05/084736, U.S. Pat. No. 5,871,007, US20050087191 and US20050126469.

Very few of the proposals have been successfully commercialised. The probable reasons for the lack of commercialisation are difficulty in manufacture, poor reliability and excessive cost.

The present invention has been made with the above points in mind.

SUMMARY OF THE INVENTION

According to the present invention there is provided a dose counting device for use with a medicinal metered dose dispensing device and for converting movement of an actuator into rotational movement of an annular member, the device comprising an actuator having at least one finger that is designed for reciprocal movement comprising an outward stroke and a return stroke, an annular member having a helical thread segment formed about a circumferential arc on a part of its surface, and a drive nut positioned around a radial cross-section of the annular member and having an internal helical rib engaged with said helical thread segment on the annular member whereby rotation of the drive nut about the circumferential arc of the annular member results in rotational movement of the annular member, the outer surface of the drive nut comprising one or more driving surfaces for engagement by said at least one finger on the actuator during said reciprocal movement to cause rotation of the drive nut.

A device in accordance with the invention is particularly advantageous in that it allows for a high gear reduction in a confined space and thus finds particular utility as a dose counter or dose indicator for an inhaler device.

As utilised as a dose counter or indicator in a pressurised metered dose inhaler (pMDI), the invention confers the advantage of occupying a small space, allowing it to be retrofitted to most existing pMDI adapter designs without the need for significant design changes. The invention thus allows the provision of an inhaler dose counter or indicator that retains the adapter shape and size and format with which patients are familiar. This contrasts with prior art dose counter or indicator designs that often require inhaler adapters to be made bulkier, causing patient unfamiliarity, obstructing the patient's nose, etc.

The device of the invention is more robust and secure than many previous worm and rack mechanisms, because the drive nut is captive around the annular member and therefore these two components cannot flex apart under load. Furthermore, when the drive nut is held in a fixed position accidental movement of the annular member is essentially prevented.

The annular member may be a continuous ring. If the ring is moulded as a single piece, the drive nut may be formed in two or more portions and assembled around a radial cross-section of the annular ring e.g. by the pieces of the drive nut being welded or glued or by mechanically interlocking the parts.

Alternatively the annular ring may be a split ring. A split ring enables the drive nut to be moulded as a single piece and the drive nut threaded over the annular member. The split ring may be manufactured as a substantially complete annulus and the abutting end parted to facilitate threading of the drive nut. Alternatively, the annular member could be shaped into the form of an annulus after assembly of the drive nut e.g. it could be made as a single helical turn of material which is flattened into a ring after assembly of the drive nut. The use of a split ring desirably provides a means for terminating the count since the drive nut can be arranged to be unable to pass over the split to begin a second rotation of the annular member. A positive end of count indication may be given by providing a projection on one end of the split ring against which the drive nut will abut when the annular member has completed its motion through the drive nut. Other means of terminating the count can be envisaged, however, such as a projection on an annular member that is in the form of a continuous ring.

In alternative embodiments the annular member does not complete a circle, but desirably comprises at least 50%, more preferably at least 75%, of the circumference of a circle.

In certain embodiments of the device, the annular member has a helical thread segment formed about a circumferential arc on a radially inner part of its surface. In such embodiments, the radially outer part of the surface of the annular member is desirably free of any helical thread segments. Indicia providing an indication of the number of doses dispensed from and/or remaining in the dispensing device (e.g. inhaler) may be provided on the radially outer surface of the annular member.

In other favourable embodiments, the annular member has a helical thread segment formed about a circumferential arc on a radially outer part of its surface. For such embodiments also, depending on the particular design of annular member, indicia, again providing information concerning the number of doses dispensed and/or remaining, may be provided on the radially outer surface of the annular member.

In embodiments where the annular member has a helical thread segment formed about a circumferential arc on a radially outer part of its surface, the radially inner surface of the annular member is preferably designed in a "cut away" fashion to form a protruding circumferential ring projecting towards the centre. This protruding circumferential ring acts as a guide for the drive nut, facilitating the rotation of the drive nut around the helical thread section and essentially eliminating any potential of the drive nut pitching or yawing.

In some preferred embodiments the annular member has a helical thread that does not go all the way around its surface (e.g. in embodiments including an annular member having a helical thread segment formed about a circumferential arc on a radially inner part of its surface, the radially outer part of its surface being free of any helical thread segments, or in embodiments including an annular member having a helical thread segment formed about a circumferential arc on a radially outer part of its surface, its radially inner surface being provided with a protruding circumferential ring projecting towards the centre), the potential of the drive nut jamming is reduced or essentially eliminated. Were the annular member to have a helical thread that goes all the way round its surface, the helical thread elements at the radially inner surface of the annular member would have to be more tightly spaced, for example, leading to a greater possibility of the drive nut jamming.

The drive nut is desirably generally cylindrical in shape having an axial bore with a helical rib protruding from the internal surface. The rib preferably comprises a single helical turn and is dimensioned to engage the helical thread segment of the annular member.

The outer surface of the drive nut comprises one or more driving surfaces for engagement by a finger on the actuator. Preferably, the drive surfaces are in the form of outwardly pointing ratchet teeth disposed around the circumference of the drive nut. In a preferred embodiment the drive nut has a smooth central cylindrical portion with a circle of ratchet teeth on either side. The ratchet teeth cause incremental rotation of the drive nut as they are engaged and pushed by the finger on the actuator. The ratchet teeth also have a second function, which is that they may be engaged by a pawl that prevents back rotation of the drive nut during the return stroke of the actuator. Thus, the annular member may be advanced by incremental rotational movement of the drive nut in response to each outward stroke of the reciprocal movement of the actuator finger.

In one configuration the actuator may comprise a flexible arcuate member that is held at one end of the arc but is free to move at the other end. The arcuate member is configured to flatten or straighten upon application of a force, thereby moving the free end. (The terms "flatten" and "straighten" are taken to include the meanings "partially flatten" and "partially straighten", respectively.) The free end of the arcuate portion may comprise a finger or nib to engage a drive surface on the drive nut. The movement of the free end may be guided by a bearing surface on the actuator configured to act upon the cylindrical surface of the drive nut. The use of such guidance is particularly advantageous since it will be appreciated that the direction of movement of the free end of the arcuate member will not be linear as the arcuate member is flattened. The apex of the arcuate member is conveniently positioned to bear against the ferrule of the aerosol valve, such that depression of the aerosol container sufficient to fire the valve will cause deformation of the arcuate member sufficient to cause the actuator to advance the drive nut. In a preferred embodiment, the actuator comprises two arcuate members spaced apart so that they may be positioned either side of the valve stem. Preferably, each arcuate member may be in the form of an arch. Each arch may have an associated finger or nib and a guide surface may be disposed between the fingers.

While the annular member could be marked to provide a visual indication of the dose count as mentioned above, the device may desirably comprise an indicator ring which is linked directly to the annular member to rotate therewith. Accordingly the indicator ring would be appropriately provided with indicia providing an indication of the number of doses dispensed from and/or remaining in the dispensing device (e.g. inhaler). Indicia may be any appropriate markings useful in visually displaying an indication of doses remaining or dispensed, such as colour bands and/or numerals to indicate every ten, twenty or other suitable number of doses or a colour or text that the device is empty, needs to be replaced, or that a refill should be obtained.

The annular member, drive nut, actuator and indicator ring may be assembled on a chassis which is constructed and arranged to be positioned within the adapter of an inhaler. The indicator ring could be positioned for viewing through the mouthpiece but preferably the adapter has a window in its wall through which the indicator ring may be viewed.

DRAWINGS

The invention will now be described with reference to the accompanying drawings in which:

FIG. 3A represents a plan view of the annular member on a larger scale than FIGS. 1 and 2, while FIG. 4A represents an end view of the drive nut on a larger scale than FIGS. 1 and 2, while FIGS. 5A and 5B represent a perspective view and an end view, respectively, of the actuator on a larger scale than FIGS. 1 and 2, while FIG. 7A represents a front elevation of a press-and-breathe inhaler incorporating the dose counter illustrated in FIGS. 1, 2 and 6, while FIG. 7B represents a cross-section along the line A-A shown in FIG. 7A, FIGS. 8A to 8C are diagrammatic views showing the interaction between the aerosol valve and certain components of the dose counter illustrated in FIGS. 1, 2, and 6 during the firing stroke of the aerosol valve of the inhaler of FIG. 7, FIGS. 9A to 9C are diagrams showing the interaction between the aerosol valve of the inhaler and certain components of the dose counter illustrated in FIGS. 1, 2, and 6 during the return stroke of the aerosol valve of the inhaler of FIG. 7, and FIG. 10A represents a horizontal cross-section through a drive nut assembled onto part of an annular member in the form of a drive wheel, while

DESCRIPTION OF PREFERRED EMBODIMENTS

Figure 1:
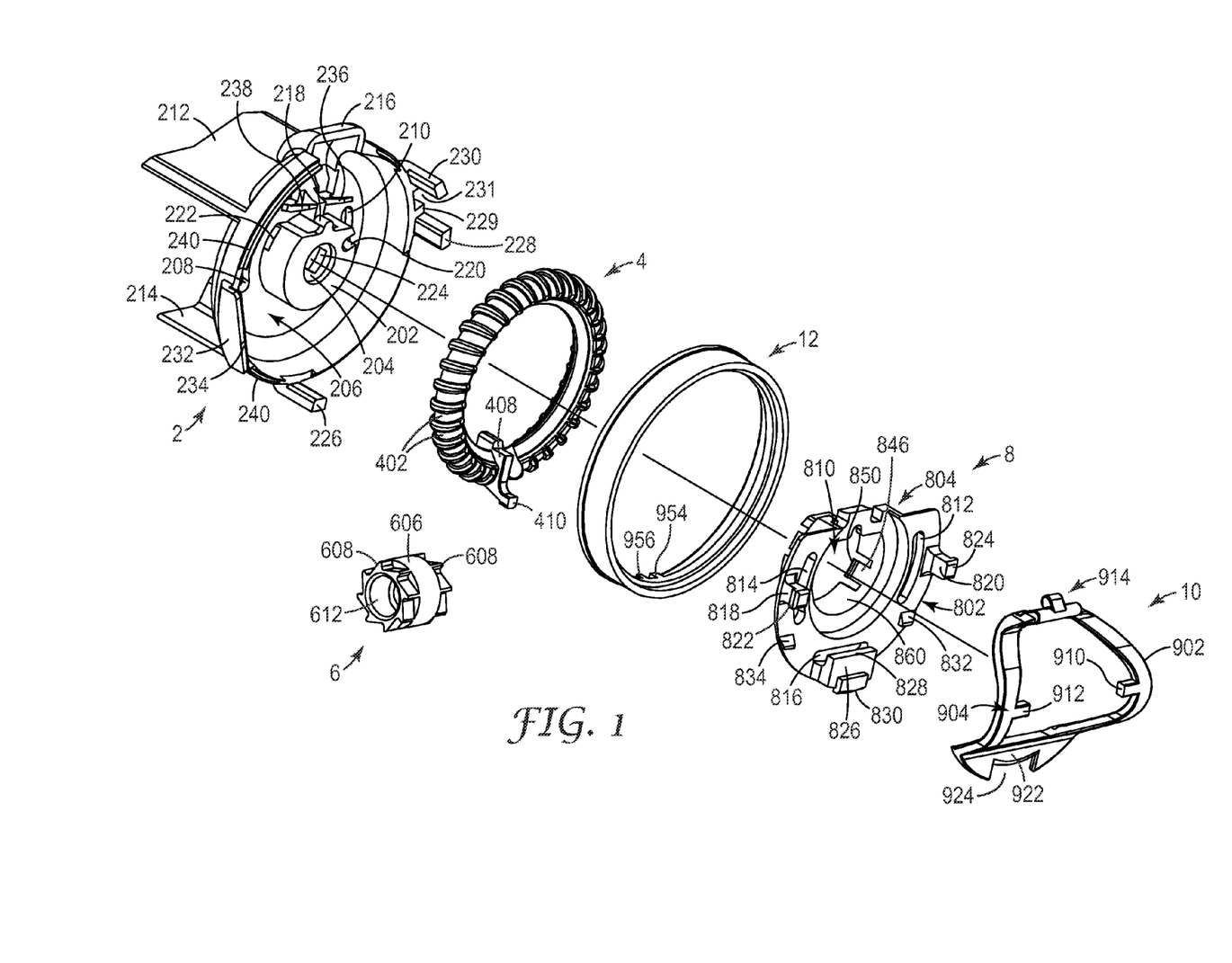
FIGS. 1 and 2 represent respective exploded views of an embodiment of a dose counter in accordance with the invention.
Figure 2:
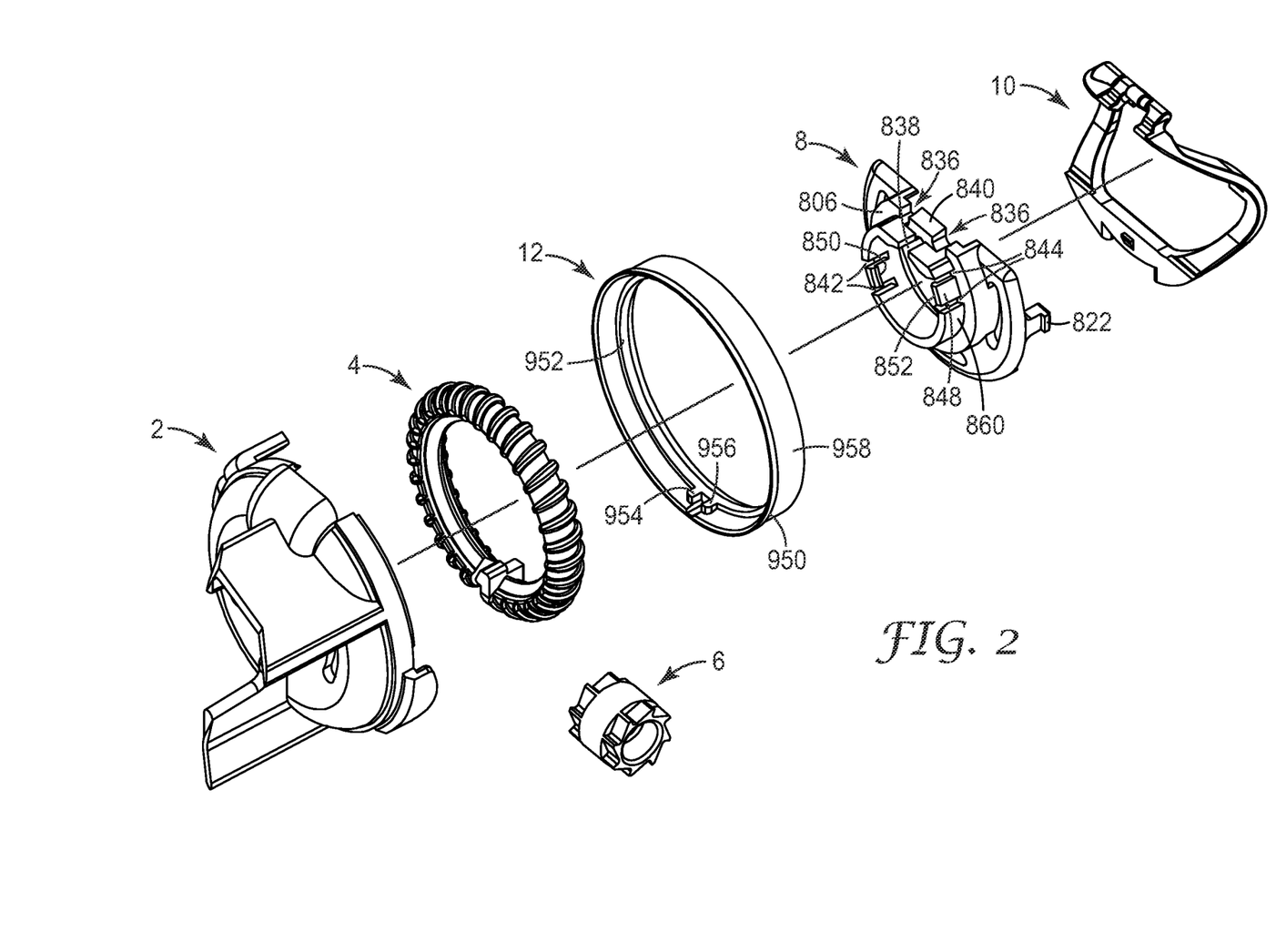
Figure 6:
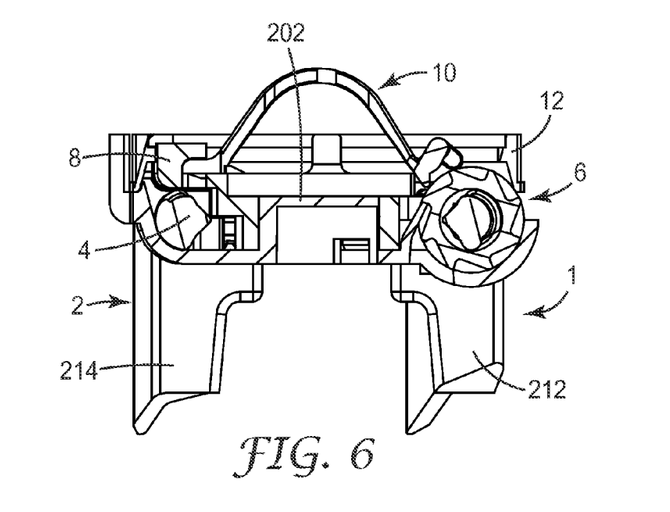
FIG. 6 represents a sectional view through the dose counter shown in FIGS. 1 and 2 assembled.

FIGS. 1, 2 and 6 illustrate an embodiment of a dose counter (1) in accordance with the invention, in particular one suitable for use with an inhaler. Terms such as 'vertical' or 'top' are to be read with reference to the orientation shown in FIG. 6. Referring to the drawings it can be appreciated that the dose counter can be desirably provided as a stand alone unit with parts assembled onto a chassis (2). The illustrated dose counter comprises an annular member in the form of a drive wheel (4), a drive nut (6) and an actuator in the form of a flexible member (10). The illustrated dose counter also comprises an indexing arm base (8) onto which one end of the flexible member (10) is held in place via loose engagement. The illustrated dose counter further includes an indicator ring (12) linked to the drive wheel (4) for rotation therewith.

The chassis (2), shown best in FIGS. 1 and 2, is shaped like a shallow bowl with a raised hollow central cylindrical boss (202) having a central hole (204), so that a circular trough (206) is formed in the bowl. The trough has two circumferential slots (208, 210); their position corresponds to those of two circumferential slots adjacent the cutaway segment of the indexing arm base, which will be described later. The chassis has two downwardly extending legs (212, 214) shaped to fix the counter stably in an adapter of an inhaler in such a position as not to interfere with the spray and to permit actuation of the counter by downward movement of the aerosol unit.

One of the legs (212) supports a cradle (216) that is formed out of part of the circumference of the bowl which is slightly lower than the rest of the bowl. The other leg (214) supports part of the trough diametrically opposite the cradle. The first leg (212) is wider and extends to a position corresponding to the side of the inside entrance to the mouthpiece of the inhaler adapter that is opposite that occupied by the second leg.

The central circular boss (202) has a vertical segment cut away apart from a remaining central vertical rib (218). A small radial slot (220) cut away from the boss just to one side of the vertical segment extends outwards from just outside the central hole, and locates onto a rib at the rear of the inhaler actuator nozzle block. Two small circumferential slots are cut away from the foot of the boss, a first slot (222) that is just to one side (the side which is opposite to the radial slot (220)) of the cut away vertical segment, and a second slot (224) diametrically opposite the first.

The bowl has three upwardly extending posts (226, 228, 230) and an upwardly extending flange (232) positioned outside its circumference and attached thereto. The upwardly extending posts are positioned to limit undue flexing of the indicator ring (12). Two of the upwardly extending posts (228, 230) are close together and between them at the bottom lies a circumferential beam (229), divided at its middle by a gap (231) just large enough to locate on an internal rib at the back the inhaler actuator. The flange (232) has an upper surface (234) to engage the innermost edge of the upper inside surface of the actuator mouthpiece. From the trough two ratchet fingers or pawls (236, 238) extend upwards and slightly outwards from near the ends of the vertical segment.

The rim of the bowl has a circumferential rebate (240) extending in parts of the rim that are spaced from the three upwardly extending posts, the upwardly extending flange and the cradle.

Figure 3A:
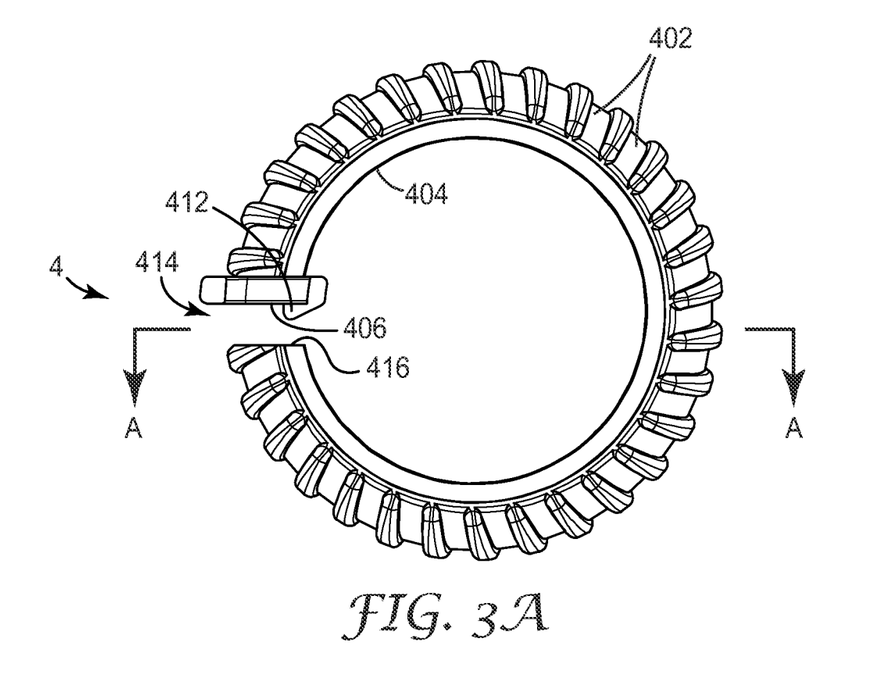
Figure 3B:
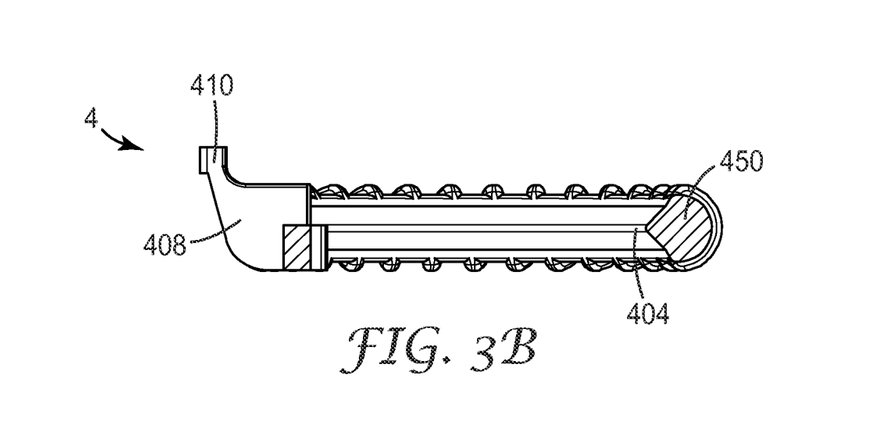
FIG. 3B represents a sectional view along the line A-A shown in FIG. 3A.

In the illustrated embodiment, the annular member having a helical thread segment formed about a circumferential arc on a part of its surface is provided in the form of a drive wheel. Herein, "circumferential arc" is taken to mean an arc of the circle that runs around, in a circumferential direction, the centre line or the approximate centre line of the annular member. For example referring to FIG. 3B showing a sectional view of the drive wheel of the exemplary embodiment, the general position of the centre line is marked as 450, while in FIG. 10A the circumferential arc is indicated with a dotted line. The drive wheel (4), shown best in FIGS. 3A and 3B, is an almost complete arc of a torus having grooves (402) shaped similar to parts of an external helix to define a helical thread segment disposed around the outer surface in a similar position to that of the tread on a tyre. The inner surface is cut away to form a protruding circumferential rim (404) projecting towards the centre, to provide two points of contact with the ends of the inner bore of a drive nut described later.

On one end (406) of the arc of the torus is an orthogonally arranged stepped plate (408) with an upwardly extending stylus (410). The plate (408) has a wedge-shaped feature (412) extending further from the end of the arc of the torus and into the region where there is a split (414) in the torus.

Figure 4A:
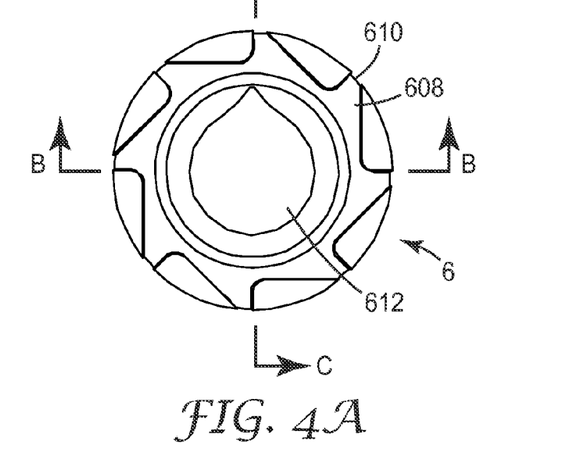
Figure 4B:
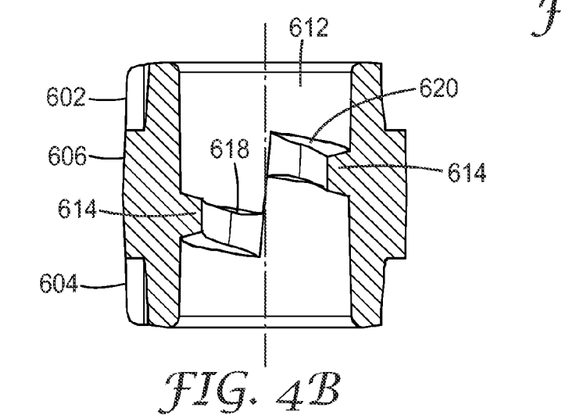
FIG. 4B represents a section along the line B-B shown in FIG. 4A and an outline view of the rib as it would be seen behind that section.
Figure 4C:
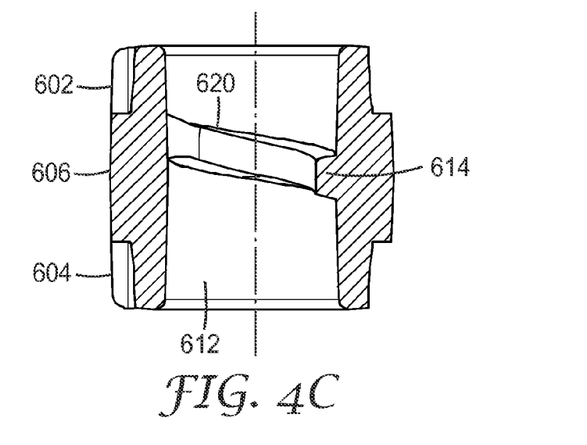
FIG. 4C represents a section along line C-C shown in FIG. 4A and an outline view of the rib as it would be seen behind that section.

The drive nut (6), shown best in FIGS. 4A, 4B and 4C, is a cylindrical component having end sections (602, 604) and a central section (606). A circle of eight outward pointing ratchet teeth (608) are disposed on the circumference of the cylinder on each end section, the teeth on one circle having the same angles as the corresponding teeth on the other circle. The central section has a smooth cylindrical surface level with the apices of the ratchet teeth as shown at (610). The cylindrical component has an axial bore (612) and the internal surface so formed has a protruding helical rib (614) in the form of a single helical turn of oblong cross-section that extends along about half the length of the drive nut and is positioned centrally along its length. FIG. 4B representing a cross section along the line B-B in FIG. 4A shows the leading (618) and trailing (620) edges of the rib as it would be seen behind the cross section. As can be appreciated from FIG. 4C, showing a cross section along line C-C shown in FIG. 4A and a view of the rib as it would be seen behind that cross section, the helical form of the leading part of the rib continues so as to link with the trailing part of the rib. The provision of such a rib having a single helical turn (i.e. one that extends for no more than 360° round, e.g. the inner bore of, the drive nut) is advantageous in that the internal helical rib is easily provided by injection moulding, without the need for screw-off release from the moulding tooling. Also the provision and use of such a single turn is favourable in that the chance that moulding dimensional variations and tolerances might cause problems with the accuracy of interaction between the drive nut (6) and the drive wheel (4) is reduced or essentially minimized.

The drive nut (6) is assembled onto the drive wheel (4) by screwing it onto the end of the drive wheel without the stepped plate (416) (see FIG. 3A). During assembly the drive nut will be screwed back again until it rests against the wedge-shaped feature (412) that is designed to position the drive nut for the start of counting. (In this start position, the drive nut is essentially bridging the gap (414) between the two ends of the drive wheel.) The drive wheel and drive nut assembly so formed will be located in the trough (206) of the chassis with the drive nut located in the cradle (216). This positioning allows substantially only the desired functional movement of the drive nut and drive wheel.

Figure 10A:
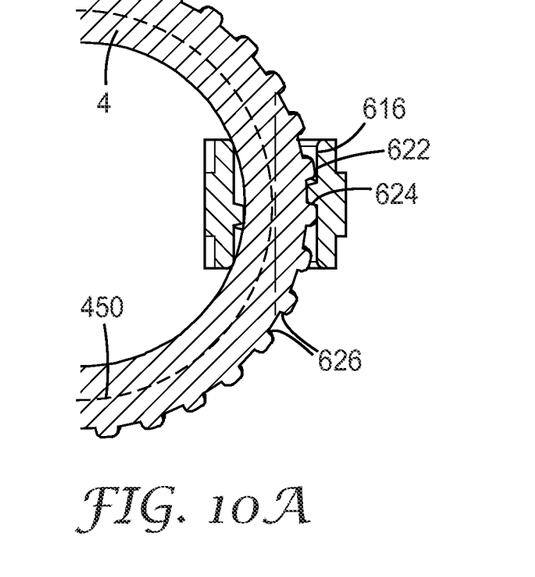
Figure 10B:
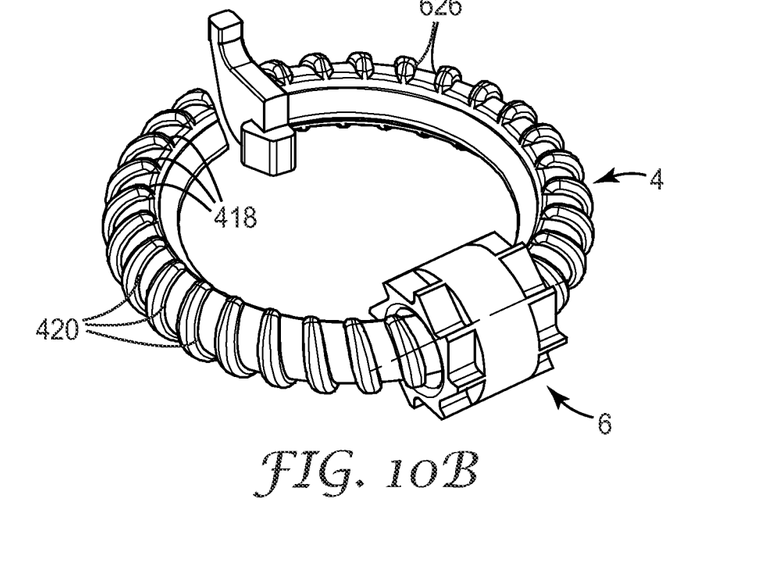
FIG. 10B represents a perspective view of a drive nut assembled onto such a drive wheel.

Referring to FIGS. 10A and 10B showing a partial horizontal cross-section and a perspective view, respectively, of the drive wheel and drive nut assembly with the drive nut already advanced along the drive wheel, it can be recognized that the outermost line (616) of the inside surface of the drive nut is straight and is tangential at its centre point to the drive wheel (best seen in FIG. 10A). The shape of each groove on the drive wheel, best seen in FIG. 10B, is favourably engineered to correspond to the volume swept out by the helical rib on the drive nut as the drive wheel traverses the drive nut, except at the ends (418) of the grooves where some lead-in is provided to facilitate initial engagement with the rib. The interaction between the drive nut and drive wheel is designed to ensure that accurate and robust location of each component is provided, in order to ensure accurate counting of doses. In particular, since the drive nut is desirably made of a rigid material for robustness, to ensure that the drive nut can rotate about the drive wheel whilst fitting closely enough for the rib (614) and a groove (402) to interact, the drive nut (6) is desirably shaped not to follow the curvature of the drive wheel. Moreover it is preferred that the drive nut be essentially cylindrical in form, as shown in FIG. 10A. As can be appreciated from FIG. 10A, the inside profile (e.g. 616) of the drive nut and the external profile (622) of the drive wheel are spaced apart towards the ends of the drive nut i.e. away from the central tangential point (624) on the drive nut relative to the drive wheel, due to the curvature of the drive wheel, and for this reason the ribs and grooves are typically made relatively deep to facilitate secure inter-engagement. Also as can be appreciated from FIG. 10A, since the rib projects radially inwardly with respect to the (straight) axis of the drive nut whilst the grooves are arranged about a circumferential arc of the drive wheel, it is desirable that each groove is slightly flared at its extremities (626). Generally the distance in the direction of the axis of the drive nut between the leading edge (618) and the trailing edge (620) of the rib (FIG. 4B) equals the distance between leading edges (420) of adjacent grooves (FIG. 10B), so that during use the rib of the drive nut locates correctly into the next groove of the drive wheel. As can be recognized from the illustrated embodiment, the rib and groove radial profiles are generally constructed and arranged to avoid the possibility of them wedging, e.g. when two parts of the rib are simultaneously engaged with adjacent grooves, whilst still ensuring that the engagement is tight enough to prevent relative wobble.

In alternative embodiments (not shown) the annular member may be provided in the form of a drive wheel, again being an almost complete arc of a torus, having grooves shaped similarly to parts of an external helix to define a helical thread segment disposed around the inner surface of the drive wheel, the radially outer part of the surface of drive wheel being free of any helical thread segments.

Returning to the illustrated embodiment, the indexing arm base (8), best illustrated in FIGS. 1 and 2, is made up of a circular section (802) with a cutaway segment (804), an open cylindrical section (806) and an inner wall section (860).

The circular section has a central hole (810) large enough to accommodate the nose of the valve ferrule. It has three circumferential slots (812, 814, 816) positioned at 90 degree intervals from the cutaway segment. Upwardly extending hooks (818, 820) with small outward barbs (822, 824) are positioned on points of the circumference of the circular section corresponding to the centres of the two circumferential slots (812, 814) adjacent the cutaway segment. A containing rim (826) is positioned on the part of the circumference corresponding to the other circumferential slot (816), having an inwardly extending flange (828) and a small outward barb (830) on its top. The two circumferential slots (812, 814) adjacent the cutaway segment and the corresponding two circumferential slots (208, 210) in the chassis are positioned radially inside the drive wheel, so that they provide a passage for the user to inhale air through the counter when installed in the inhaler actuator. Two small ramps (832, 834) are positioned on the perimeter of the circular section about midway between the containing rim (826) and each upwardly extending hook (818, 820).

The open cylindrical section (806) is open at both ends and extends downwardly from the circular section. It has a flat side corresponding to the cutaway segment of the circular section apart from two parts (836) recessed either side of a small bridge (840) joining the two parts around a vertical groove (838) described later.

The inner wall section (860) extends downwardly from an inner part of the cylindrical section and is similarly shaped to this part of the cylindrical section so that it has a gap (838) below the small bridge (840). It also has two diametrically opposite pairs of gaps (842, 844) each surrounding a small section of wall (846, 848) with inner barbs (850, 852) at the ends, to clip into the corresponding small circumferential slots (222, 224) in the chassis thereby fixing the indexing arm base to the chassis.

Both such downwardly extending parts therefore accommodate, centrally to the cutaway segment of the circular section, an internal vertical groove (838). It will be appreciated that the structure of these two parts described above provides space for the ratchet fingers (236, 238) on the chassis to operate through those sections of the indexing arm base. The inner wall section (860), inner surface of the open cylindrical section (806) and vertical groove (838) are dimensioned to fit over the hollow raised central cylindrical boss (202) of the chassis and its vertical rib (218), so that the circular section retains the drive wheel.

Figure 5A:
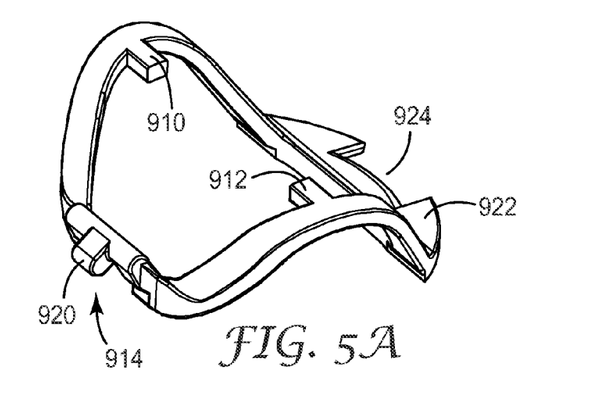
Figure 5B:
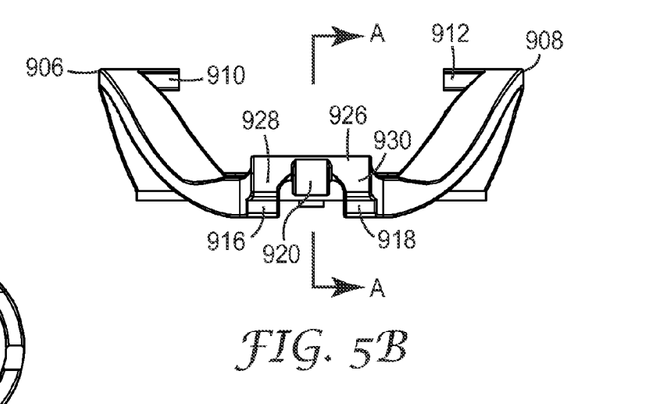
Figure 5C:
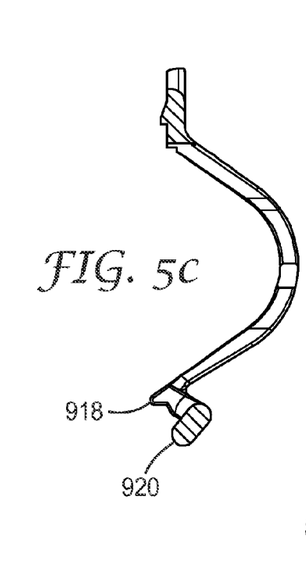
FIG. 5C represents a section along the line A-A shown in FIG. 5B.

As can be best appreciated from FIGS. 1, 2 and 5, the actuator is desirably in the form of a flexible member (10) comprising two opposed thin arcuate members (902, 904) spaced apart relative to a central vertical plane of symmetry and with their apices (906, 908) positioned outwardly. Each apex has a short pier (910, 912) extending inwardly, to increase the land area for engagement with the valve ferrule of the aerosol container. Each end of each arcuate member is joined to a respective end of the other arcuate member at the front, by a drive structure (914) comprising two fingers or nibs (916, 918), one on either side of a bearing surface (920), and at the rear by a horizontal beam (922) having a section (924) cut away from the rear. Being joined at both ends confers stability to the thin arcuate members.

The bearing surface (920) is arranged on the underside of a rectangular bridge (926) with parapets (928, 930), the nibs (916, 918) being at the feet of the parapets where they meet the feet of the arches. The nibs are sharp by design to engage the ratchet teeth (608) on the drive nut (6). The bearing surface (920) is designed to engage the smooth cylindrical surface (606) of the drive nut. The horizontal beam (922) is held in place by loose engagement with the inwardly extending flange (828) of the containing rim (826) and by the two ramps (832, 834) on the indexing arm base (8).

Indicia providing an indication of the number of doses dispensed or remaining may be provided on the radially outer surface of the drive wheel. For example referring to the illustrated drive wheel indicia could be appropriately provided between the helical thread segments. Alternatively, as shown in the illustrated embodiment, the dose counter may be provided with an indicator ring.

In the illustrated embodiment, the indicator ring (12) is essentially ring-shaped (see FIGS. 1 and 2). It comprises a small outer rim (950) extending outwards at the bottom and an inner rim (952) extending inwards about half way up the inside surface. There are two short downward ribs (954, 956) a small distance apart extending from the inner rim. The downward ribs are designed to contain the upwardly extending stylus (410) of the drive wheel (4), which consequently drives the indicator ring round as it moves. The inner rim is designed to be engaged by the three outward barbs (822, 824, 830) of the indexing arm base. The indicator ring (12) is prevented from flexing away from this engagement by the three posts (226, 228, 230) and the flange (232) upwardly extending from the chassis (2). The outer surface (958) of the indicator ring is typically provided with indicia (not shown).

Assembly

Figure 7A:
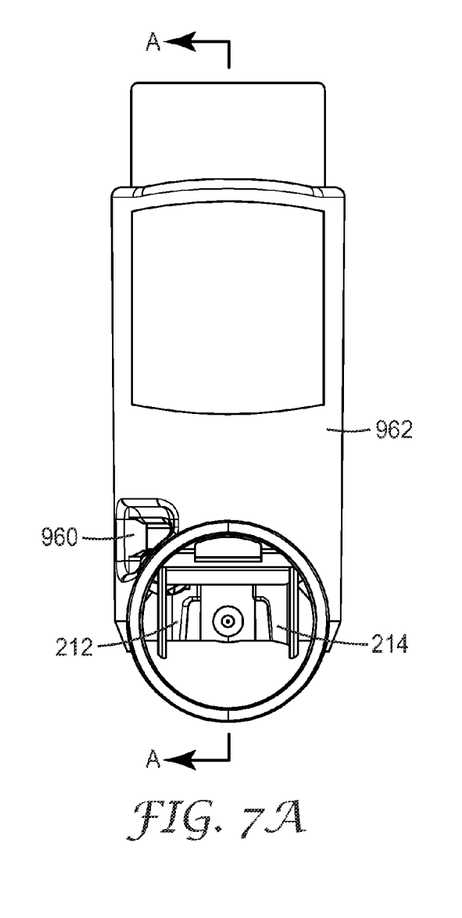
Figure 7B:
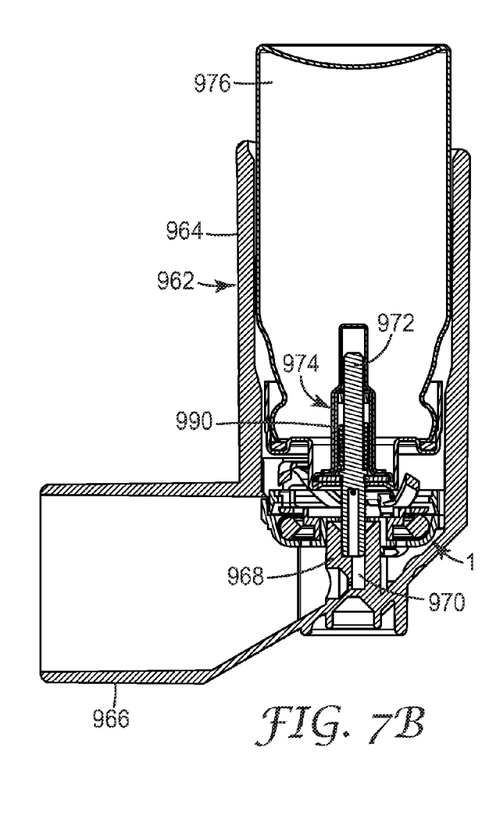

The chassis (2), drive wheel (4), drive nut (6), indexing arm base (8), flexible member (10) and indicator ring (12) are assembled as described above. FIG. 6 provides an illustration of a sectional view through the assembled dose counter. Referring to FIG. 7, the assembled dose counter can be placed in the body of an aerosol adapter (962) which comprises a sleeve (964), mouthpiece (966) and nozzle block (968) having an aperture (970) to accommodate the valve stem (972) of the valve (974) of an aerosol vial (976). The dose counter (1) generally is positioned within the adapter so that the nozzle block is accommodated within the central hole (204) of the chassis with the legs (212, 214) of the chassis positioned either side of the spray path from the nozzle block to the mouthpiece. A window (960) may be positioned in the vertical section of the inhaler adapter to the user's left near the join between its sleeve and mouthpiece sections, so that a short length of the outer surface of the indicator ring of the dose counter together with the indicia provided on the indicator ring are visible therethrough. Alternatively, the window may be positioned elsewhere round the inhaler adapter. With the exception of the window, the aerosol adapter is of substantially conventional design for a press-and-breathe inhaler.

Mode of Operation

Figure 8A:
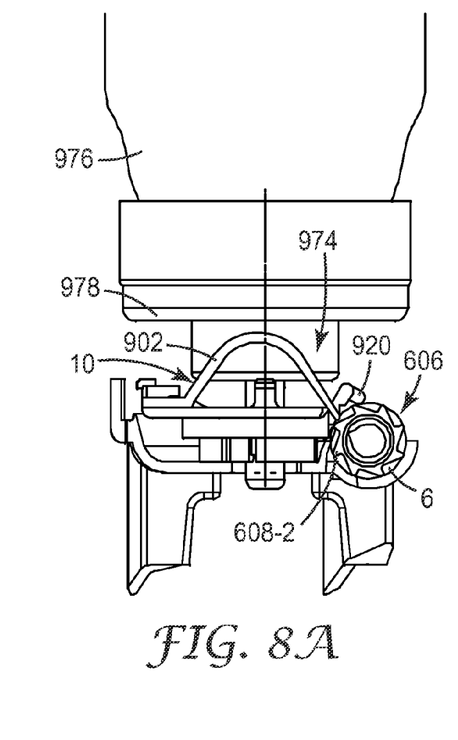
Figure 8B:
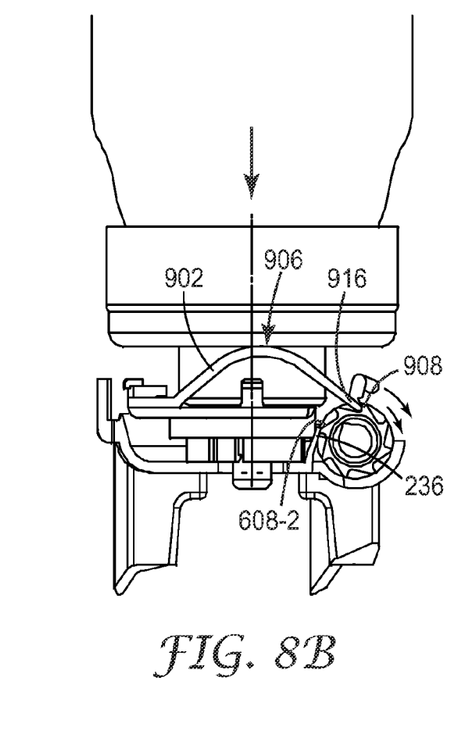
Figure 8C:
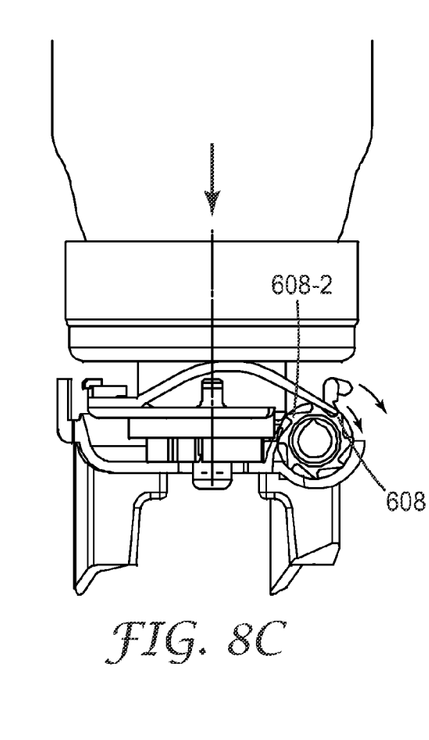
Figure 9A:
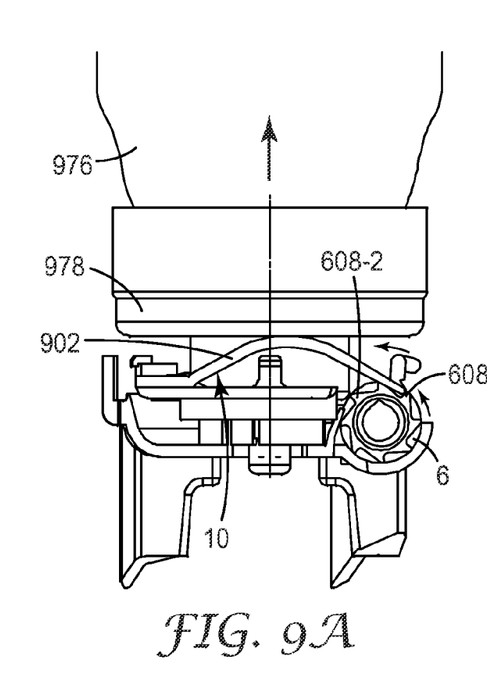
Figure 9B:
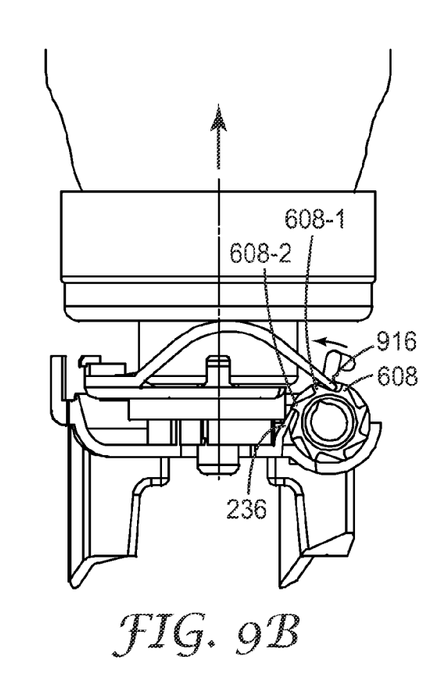
Figure 9C:
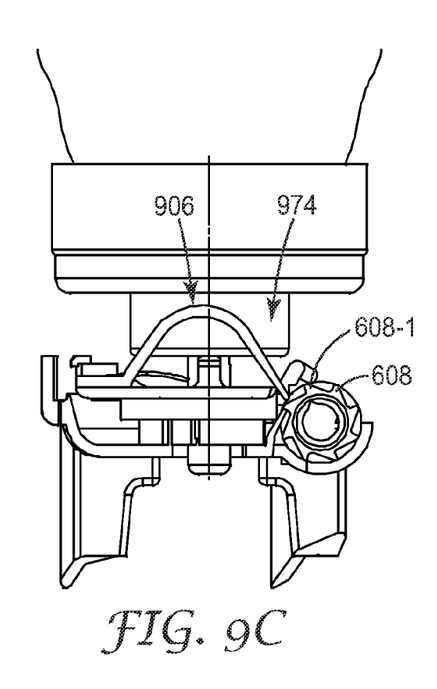

FIGS. 8 and 9 provide diagrammatic views showing the interaction between the aerosol valve (974), in particular the valve ferrule (978), and certain components of the dose counter, in particular the flexible member (10), and the drive nut (6), during the firing stroke (FIGS. 8B and 8C) and during the return stroke (FIGS. 9A and 9B) and at rest prior to the firing stroke (FIG. 8A) and after the return stroke (FIG. 9C). For ease of viewing in both FIGS. 8 and 9 the complete dose counter is not drawn, nor is the aerosol adapter. Movement of the respective components is represented by arrows in the Figures.

When the user operates the inhaler to fire a dose of medicament, the valve ferrule (978), moving downwardly with the aerosol vial (976), engages the apices (906, 908, the latter not visible) and piers (910, 912, not visible) of the flexible arcuate members (902, 904, the latter not visible) (FIG. 8B) and pushes the flexible arcuate members downwards (FIGS. 8B to 8C). Since, as already explained in detail above, the flexible member is held at one end by a loose engagement with the indexing arm base (not shown), the downward pressure causes the flexible arcuate members to flatten, causing the bearing surface (920) of the flexible member to move over the smooth central surface (606) of the drive nut (6) and the nibs (916, 918, the latter not visible) of the flexible member to engage with a tooth (608) on each side of the drive nut to rotate the drive nut about its axis (FIG. 8B to FIG. 8C). The drive nut is driven slightly beyond a point at which the ratchet fingers (236, 238, the latter not visible) on the chassis ride over the ratchet teeth (608-2) two positions behind the ratchet teeth (608) engaged by the nibs of the flexible member. (Compare FIGS. 8A and 8B.)

It will be appreciated from FIGS. 8A to 8C, that in order for the flexible arcuate members to provide sufficient travel to operate on the ratchet in a sufficiently large increment, even though the reciprocal motion and distance is small, the flexible arcuate members are favourably provided with an arch that is fairly steep in the rest position (FIG. 8A). Use of such a steep arch could result in very steep operation of the nibs of the flexible member against the teeth of the drive nut, resulting in high frictional forces relative to the resolved tangential component of the rotational driving force. However, as mentioned above, the use of a bearing surface of the flexible member positioned to bear on the central cylindrical portion of the drive nut is advantageous in this regard, because the nibs of the flexible member are thus guided into a more tangential motion against the ratchet, reducing the angle at which the nibs operate against the ratchet and hence helping to overcome frictional force. It will also be appreciated that if excess reciprocal motion of the aerosol vial occurs (e.g. due to valve dimensional tolerance ranges), it can readily be absorbed by the dose counter mechanism, as further motion of the nibs (916, 918, the latter not shown) may continue in a largely horizontal direction without significant unwanted further rotation of the drive nut.

Although not shown in FIG. 8, it will be appreciated that the axial movement of the drive nut is converted, by engagement of the helical rib (614) of the drive nut with the grooves (402) of the helical thread segment of the drive wheel (4), to rotational movement of the drive wheel (4) about its axis, which then, by engagement of the upwardly extending stylus (410) of the drive wheel with the ribs (954, 956) of the indicator ring (12), drives the indicator ring (12) round a short distance.

After firing a dose of medicament, e.g. when the user releases manual pressure on the inhaler, the aerosol vial (976) will return to its rest position (FIGS. 9A through 9B to 9C) under the influence of its valve's internal return spring (990, shown in FIG. 7B) causing an upward movement of the valve ferrule (978) and allowing the flexible arcuate members (902, 904, the latter not visible) to return to their former shape until finally the valve ferrule disengages completely from the apices (906, 908, the latter not visible) of the flexible arcuate members (FIG. 9C). As the valve ferrule and the apices of the flexible arcuate members are moving upwardly, the nibs (916, 918, the latter not visible) of the flexible member ride over a tooth (608-1) on each side of the drive nut; i.e. the teeth next in line to those just previously advanced (608) during the firing stroke (compare FIGS. 9B and 9C). Reverse movement of the drive nut is controlled by engagement between the two ratchet fingers (236, 238, the latter not visible) on the chassis and ratchet teeth (608-2) further round the drive nut (6). (Compare FIGS. 9A and 9B.) The angle between the ratchet fingers and the ratchet teeth surfaces against which they ride, and the force applied by the ratchet fingers are typically designed such that the drive nut is allowed to move slightly in reverse and/or the ratchet fingers drive the drive nut slightly in reverse until the fingers rest in a gullet of the ratchet teeth of the drive nut (again, compare FIGS. 9A and 9B) preventing further back rotation of the drive nut during the remaining movement of the flexible arcuate members back to their rest position (FIG. 9C).

Components of devices, e.g. dose counter devices, described herein may be made of plastics material, particularly thermoplastics material, and may be produced by injection moulding. The indicator ring, chassis, drive nut and drive wheel and indexing arm base may be constructed of rigid plastics materials. The resiliently flexible portion of the flexible member may be constructed of an appropriate plastics material e.g. polypropylene or polybutylterephthalate (PBT). The flexible member may optionally be made from more than one material, for example by two shot moulding. For example, a fairly flexible plastic material may be used for the flexible arcuate members (902, 904) and a different, more rigid, plastic may be use for other parts of the flexible member (10). Alternatively, the flexible member may be made by insert moulding of plastic parts onto a metal wire frame. The dimensions and thicknesses of the flexible member, along with the choice of materials for different parts of it to achieve the desired flexibility, resilience or rigidity, may be selected to optimise the force characteristics and thereby optimise reliable counting. In addition, the materials and design may be selected to optimise the component's elasticity (recovery of shape) properties and their functional use. For example by making the flexible member of sufficiently thin arcuate sections, it can be rigid enough due to its arch-like shape to convey enough force to rotate the drive nut and drive wheel and, if applicable, an indicator ring through life, yet collapse when a (atypical) greater force is applied, such as in situations where the user needs to dispense a dose in an emergency or panic situation. For example, the dose counter device may be designed such that when the device indicates the end of life of the inhaler, the drive nut may be tight against the stepped plate on the drive wheel so that further relative motion is prevented, which prevents further rotation of the drive nut. In designs where the flexible member is designed to collapse or crush down when the user attempts to dispense further doses, even though the dose counter or indicator indicates the end of life of the inhaler, the counting device does not prevent further doses being dispensed if any doses are still remaining in the inhaler.

Dose counter devices described herein are advantageous in that existing inhaler designs can be easily retrofitted with such counter devices with only a minimum of changes to the design of the inhaler itself (generally simply the inclusion of a viewing window in the adapter and possibly dose counter retention clipping features). Additionally, dose counter devices described herein are robust and much more "tolerance-insensitive" than previously proposed inhaler counting devices. Also dose counting devices described herein are attractive due to their versatile design in that these dose counting devices can be easily modified for a broad range of different inhalers often by changing a single component, the flexible member. This is also advantageous in terms of development costs and resources as well as manufacturing costs (stocking, processing, logistics etc).

The invention claimed is:

1. A dose counting device for use with a medicinal metered dose dispensing device and for converting movement of an actuator into rotational movement of an annular member, the device comprising
an actuator having at least one finger that is designed for reciprocal movement comprising an outward stroke and a return stroke,
an annular member having a helical thread segment formed about a circumferential arc on a part of its surface, and
a drive nut positioned around a radial cross-section of the annular member and having an internal helical rib engaged with said helical thread segment on the annular member whereby rotation of the drive nut about the circumferential arc of the annular member results in rotational movement of the annular member, the outer surface of the drive nut comprising one or more driving surfaces for engagement by said at least one finger on the actuator during said reciprocal movement to cause rotation of the drive nut.

2. A device as claimed in claim 1, in which the helical thread segment is formed about the circumferential arc on a radially outer part of the annular member surface and/or a radially inner surface of the annular member is cut away to form a protruding circumferential ring projecting inwardly.

3. A device as claimed in claim 1 in which the helical thread is formed about the circumferential arc on a radially inner part of the annular member surface.

4. A device as claimed in claim 3 in which a radially outer part of the surface of the annular member is free of any helical thread segments.

5. A device as claimed in claim 1 in which the annular member is a continuous ring or a split ring.

6. A device as claimed in claim 1 in which the internal helical rib of the drive nut is in the form of a single helical turn.

7. A device as claimed in claim 1 in which the driving surfaces of the drive nut are in the form of outwardly pointing ratchet teeth disposed around the circumference of the drive nut.

8. A device as claimed in claim 7 in which the drive nut comprises a central cylindrical portion with a circle of said ratchet teeth on either side; and/or the device additionally comprises a pawl engageable with the ratchet teeth to prevent or restrict back rotation of the drive nut during the return stroke of the actuator.

9. A device as claimed in claim 1 in which the actuator comprises a flexible arcuate member which is held at one end, the other end being free to move, and in which reciprocal movement is caused by application and removal of a force which flattens or partially flattens the curvature of the arcuate member.

10. A device as claimed in claim 9 in which the actuator comprises a pair of said flexible arcuate members each having a finger at the free end for engagement with a respective circle of ratchet teeth.

11. A device as claimed in claim 10 in which the actuator comprises a bearing surface disposed between the two arcuate members, positioned to bear on a central cylindrical portion of the drive nut.

12. A device as claimed in claim 1 in which indicia are provided on a radially outer surface of the annular member; said indicia providing an indication of the number of doses dispensed from and/or remaining in the dispensing device; or the device additionally comprises an indicator ring linked to the annular member for rotation therewith.

13. A device as claimed in claim 1 in the form of a dose counter or indicator for an inhaler, in which the dose counter or indicator is positioned within an adapter of an inhaler.

14. A device as claimed in claim 1 in which the inhaler comprises an aerosol vial equipped with a valve and reciprocal motion of the actuator is caused by movement of the aerosol vial to fire the valve.

15. A device as claimed in claim 14 in which the aerosol valve comprises a valve ferrule which contacts the actuator when the aerosol vial is moved to fire the valve.

* * * * *